US005487887A

United States Patent [19]
Benfatto

[11] Patent Number: 5,487,887
[45] Date of Patent: Jan. 30, 1996

[54] CLEAR ANTIPERSPIRANT ROLL-ON COMPOSITIONS

[75] Inventor: Anthony Benfatto, North Brunswick, N.J.

[73] Assignee: Bristol-Myers Squibb Company, New York, N.Y.

[21] Appl. No.: 144,777

[22] Filed: Oct. 28, 1993

[51] Int. Cl.$^6$ .............................. A61K 7/34; A61K 7/38; A61K 9/10; A61K 9/107
[52] U.S. Cl. ............................. 424/66; 424/68; 514/938
[58] Field of Search ...................... 424/66, 68; 514/938

[56] References Cited

U.S. PATENT DOCUMENTS

| 4,264,586 | 4/1981 | Callingham | 424/68 |
|---|---|---|---|
| 4,499,069 | 2/1985 | Krafton | 424/66 |
| 4,788,001 | 11/1988 | Narula | 252/312 |
| 4,937,069 | 6/1990 | Shin | 424/66 |
| 5,069,897 | 12/1991 | Orr | 424/66 |
| 5,098,698 | 3/1992 | Kawam et al. | 424/66 |
| 5,162,378 | 11/1992 | Guthauser | 514/785 |
| 5,194,262 | 3/1993 | Goldberg et al. | 424/401 |
| 5,213,799 | 5/1993 | Goring et al. | 514/938 |
| 5,225,188 | 7/1993 | Abrutyn et al. | 424/66 |

OTHER PUBLICATIONS

International Cosmetic Ingredient Dictionary 1993, 5th edition, vol. I, pp. 4 and 5.
Witco Tech. Bull., Formula 101A, no date thereon.
Reheis Tech Data, Clear Water–In–Oil Antiperspirant Roll–On, no date thereon.

*Primary Examiner*—Dale R. Ore
*Attorney, Agent, or Firm*—Charles J. Zeller

[57] ABSTRACT

The present invention provides for roll-on antiperspirant compositions and more particularly concerns antiperspirant compositions which are clear and, when applied to the human skin, do not leave a visible white residue after drying. The present invention is also particularly concerned with the preparation of clear antiperspirant roll-on compositions which are stable under varying temperature conditions and also provide a suitable cosmetically acceptable feel or sensation when applied to the human skin.

26 Claims, No Drawings

CLEAR ANTIPERSPIRANT ROLL-ON COMPOSITIONS

FIELD OF THE INVENTION

The present invention relates to the field of roll-on antiperspirant compositions and more particularly concerns antiperspirant compositions which are clear and, when applied to the human skin, do not leave a white residue after drying. The present invention is also particularly concerned with the preparation of clear antiperspirant roll-on compositions which are stable under varying temperature conditions and also provide a suitable cosmetically acceptable feel or sensation when applied to the human skin.

Specifically, the present invention is directed to clear oil-in-water microemulsion based compositions containing an antiperspirant active component. In a preferred embodiment of the present invention, an antiperspirant composition comprising a particular class of organic nonresinous thickening agents in combination with the aforesaid basic ingredients is taught, which, when admixed, serve to provide a unique composition having a particularly advantageous combination of characteristics when applied to the human skin.

BACKGROUND OF THE INVENTION

The preparation of oil-in-water emulsion based compositions is generally known to the art, but not in the context of their use in preparing a clear low residue antiperspirant composition.

Over the years various workers in the field have attempted to create enhanced antiperspirant emulsion compositions using a variety of ingredients in various combinations all of which have been found to be limited in one respect or another. Amongst the prior art references relating to this area of which the applicant is aware, are the following:

U.S. Pat. No. 4,788,001 to Narula broadly discloses stable oil-in-water emulsion based compositions as containing an oil, water, and a nonionic three-component emulsifying system, each nonionic surfactant being present in stated concentrations and having a specific HLB requirement. While antiperspirant compositions are not specifically taught by this reference, Narula suggests that the oil-in-water emulsions taught there may find utility in antiperspirant compositions.

U.S. Pat. No. 4,264,586, which issued to Callingham discloses an antiperspirant emulsion composition containing an antiperspirant active, a wax, polydimethylsiloxane, water and an emulsifier.

Witco Tech. Bull. Formula 101A is directed to a clear microemulsion antiperspirant composition containing a mixture of various nonionic surfactants. The composition has a viscosity of 500–5000 cps, and is stable at elevated temperatures.

U.S. Pat. No. 4,499,069 to Krafton is directed to a specific emulsifier system containing PEG (21) stearyl ether.

The foregoing prior art references do not teach or even suggest the totality of the composition of the present invention, nor its equivalents. Further, the known prior art lacks any specific teaching as to the benefits to be achieved by utilizing the particular combination of basic ingredients taught by the applicant herein in order to achieve a clear low residue antiperspirant composition.

SUMMARY OF THE INVENTION

The present invention is directed to roll-on antiperspirant compositions and more particularly to antiperspirant compositions which are clear and which do not leave a visible white residue after drying, when applied to the human skin. In the preferred embodiment, the present invention is particularly concerned with the preparation of clear low residue forming antiperspirant roll-on compositions which are stable under varying temperature conditions and which also provide a suitable cosmetically acceptable feel or sensation when applied to the human skin.

More particularly, the present invention is directed to clear oil-in-water microemulsion based compositions containing an antiperspirant active component. In one preferred embodiment of the present invention, an antiperspirant composition comprising a particular class of organic nonresinous thickening agents in combination with the aforesaid basic ingredients provides a unique composition having a particularly advantageous combination of desirable characteristics, when applied to the skin.

Generally speaking, the clear oil-in-water emulsion compositions which are the subject of the present invention are characterized by the following combination of essential components:

(a) from about 5 to about 30 wt. % antiperspirant active;
(b) from about 35 to about 60 wt. % water;
(c) from about 5 to about 25 wt. % PEG-7-glyceryl cocoate;
(d) from about 0.5 to about 3 wt. % of an emollient, preferably isopropyl myristate;
(e) from about 3 to about 7 wt. % cyclomethicone.

The preferred compositions of the present invention may be generally characterized by the following combination of components:

(a) from about 5 to about 30 wt. % antiperspirant active;
(b) from about 35 to about 60 wt. % water;
(c) from about 5 to about 25 wt. % PEG-7-glyceryl cocoate;
(d) from about 0.5 to about 3 wt. % of an emollient, preferably isopropyl myristate;
(e) from about 3 to about 7 wt. % cyclomethicone,
(f) an organic, organic nonresinous thickener such as PEG-150 pentaerythritol tetrastearate in an amount sufficient to provide a composition viscosity of from about to about 5000 cps, generally from about 0.1 to about 3 wt. %;
(g) an oil-in-water emulsifying system comprising, in the preferred composition,
  (i) 0.5–3.0 wt. % Poloxomer 217 (polyoxyethylene, polyoxypropylene block polymer of the general formula

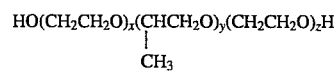

in which the average values of x, y, and z are respectively 52, 35 and 52),
  (ii) 0.5–3.0 wt. % glycereth-7-benzoate, and
  (iii) less than 5 wt. % of a nonionic surfactant for high temperature stability, e.g., octoxynol-9 (Polyoxyethylene(9) Octyl Phenyl Ether or lauricdiethanolaminde;
(h) 0.01–0.5 wt. % of a soluble electrolyte as a viscosity control agent and to enhance clarity, preferably sodium chloride;

(i) 0.5–10 wt. % of a humectant for low temperature stability, e.g., a mono- or dialkylene glycol of up to eight carbon atoms, especially dipropylene glycol, and (j) optional ingredients such as perfumes, fillers, etc., typically each in an amount of less than 1.0 wt. %.

While various prior art antiperspirant compositions may include some of the components which are also included in the antiperspirant compositions of the present invention, the presence of PEG-7 glyceryl cocoate (Cetiol HE) is unique to the compositions of the present invention and is critical to the preparation of the claimed antiperspirant compositions, which are characteristically clear and leave no visible white residue upon drying, after being applied to the human skin.

DETAILED DESCRIPTION OF THE INVENTION

As noted previously, it has been found that the combination of an roll-on antiperspirant active ingredient with a particular class of organic nonresinous thickeners and a particular type of oil-in-water emulsifying system together with various other ingredients serves to provide a clear antiperspirant roll-on composition having a particularly advantageous combination of properties, not heretofore available in the art.

As used throughout this disclosure, the phrase "non-visible residue" means that upon drying substantially no residue remains, which might be visible to the human eye.

The desirable objective of producing a clear antiperspirant composition which does not leave a visible residue after drying when applied to the human skin and has a suitable cosmetically acceptable feel to the user while at the same time providing a stable composition under diverse temperature conditions is achieved by preparing a mixture of:

(a) from about 5 to about 30 wt. % antiperspirant active;

(b) from about 35 to about 60 wt. % water;

(c) from about 5 to about 25 wt. % PEG-7-glyceryl cocoate;

(d) from about 0.5 to about 3 wt. % of an emollient, preferably isopropyl myristate;

(e) from about 3 to about 7 wt. % cyclomethicone.

In addition to the foregoing five basic components which are required in order to obtain an acceptable clear antiperspirant composition which leaves substantially no white residue after drying when applied to the human skin, one may also add a number of other non-essential ingredients in order to improve the overall qualities of shelf-life, stability and cosmetic feel, in formulating the specific antiperspirant compositions of the preferred embodiments.

Additional, non-essential ingredients may also be added to provide fragrance or to impart other cosmetic effects to the resultant antiperspirant compositions as will be apparent to one skilled in this art.

The preferred antiperspirant compositions of the present invention are prepared by blending the following combination of components:

(a) from about 5 to about 30 wt. % antiperspirant active;

(b) from about 35 to about 60 wt. % water;

(c) from about 5 to about 25 wt. % PEG-7-glyceryl cocoate;

(d) from about 0.5 to about 3 wt. % of an emollient, preferably isopropyl myristate;

(e) from about 3 to about 7 wt. % cyclomethicone;

(f) an organic nonresinous thickener, such as PEG-150 pentaerythritol tetrastearate, in an amount to provide a composition viscosity of from about 500 to about cps, generally from about 0.1 to about 3%;

(g) an oil-in-water emulsifying system comprising,
(i) 0.5–2.0 wt. % Poloxomer 217 (polyoxyethylene, polyoxypropylene block polymer of the general formula

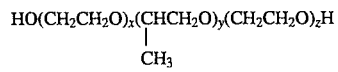

in which the average values of x, y, and z are respectively 52, 35 and 52), (ii) 0.5–2.0 wt. % glycereth-7-benzoate, and (iii) less than 5 wt. % of a nonionic surfactant for high temperature stability, e.g., octoxynol-9 (Polyoxyethylene(9) Octyl Phenyl Ether) or lauricdiethanolamide;

(h) 0.01–0.5 wt. % of a soluble electrolyte as a viscosity control agent and to enhance clarity, preferably sodium chloride;

(i) a humectant for low temperature stability, e.g., a mono- or dialkylene glycols of up to eight carbon atoms, especially dipropylene glycol, generally in amounts of from about 0.5 to about 10 wt. % and (j) optional ingredients such as perfumes, fillers, etc., typically each in an amount of from about 0.01 to about 1.0 wt. %.

The antiperspirant compositions which are the subject of the present invention comprise an antiperspirant active ingredient which may be any one of a number of known and currently commercially available antiperspirant salts. The antiperspirant active will preferably be selected from aluminum zirconium salts or aluminum chlorohydrates. Most preferably the antiperspirant active ingredient used in the compositions of the present invention will be either aluminum zirconium tetrachlorohydrex Gly or aluminum chlorohydrate. The aforesaid preferred antiperspirant active ingredients are both commercially available from industry known chemical suppliers and are generally sold in 35% and 50% solutions in water. It has been found that the antiperspirant active ingredients may be effectively employed in the compositions of the present invention in amounts from about 5% to about 30% by weight of the active ingredient.

In formulating the overall antiperspirant composition, water will be present in the overall amount of from about 35% to about 60% by weight, including the amount of water which is added with the antiperspirant active salt solution as well as the additional deionized water which is added in order to make up the final antiperspirant microemulsion.

The third essential ingredient, PEG-7-glyceryl cocoate, is a commercially available product produced by Henkel and available under the trade name Cetiol HE. This material is a clear low viscosity ingredient which, according to the manufacturer, is a self-emulsifying oil suitable for blending with most fatty raw ingredients. Cetiol HE has been recommended by its manufacturer Henkel for use where emolliency is required in aqueous formulations such as shampoos and bubble baths where it has been found to improve skin softness and feel.

While no other particular ingredient comparable to Cetiol HE has been identified, it is nonetheless anticipated that other chemically similar components which might exhibit the same chemical characteristics as Cetiol HE will also be appropriate substitutions for PEG-7-glyceryl cocoate in preparing the clear antiperspirant compositions of the present invention.

PEG-7-glyceryl cocoate has been found to be effective in preparing the compositions of the present invention in amounts of from about 5% by weight to about 25% by weight. Preferably this component will be employed in amounts of from about 15 wt. % to about 18 wt. % based upon the total weight of the antiperspirant micro emulsion produced.

The fourth essential ingredient of the clear antiperspirant microemulsion of the present invention is an emollient material, which is a fatty acid ester, such as an isopropyl stearate, preferably isopropyl myristate, or an equivalent. Isopropyl myristate is an ester of isopropyl alcohol and myristic acid. This material is commercially available under a number of trade names from a variety of commercial sources as will be known to one skilled in this art.

It has been found that the emollient component, preferably isopropyl myristate, may be effectively employed in the compositions of the present invention in amounts of from about 0.5 to about 3 wt. %. Preferably this component will be employed in amounts of about 2 wt. % based upon the total weight of the resultant microemulsion produced.

The fifth essential ingredient of the present invention, cyclomethicone, is a cyclic demethyl polysiloxane compound that is well known to the art and available from a number of commercial sources. Cyclomethicone is effectively employed in amounts of from about 3 to about 7 wt. % and preferably will be employed in amount of about 5 wt. % based upon the total weight of the final microemulsion produced.

In the preferred embodiments of the present invention in order to produce a clear antiperspirant micro emulsion having enhanced feel and other cosmetic attributes, it has been found that a number of additional components may be effectively employed. In particular, it has been found that the use of an organic nonresinous thickener in order to provide a resultant antiperspirant microemulsion composition having a viscosity of from about 500 to about 5000 CPS is highly desirable.

In carrying out the preparation of the preferred embodiments of the present invention, the organic nonresinous thickener employed is preferably PEG-150 pentaerythritol tetrastearate, which is a commercially available material known to those skilled in the art.

Generally speaking from about 0.1 to about 3 wt. % of organic nonresinous thickeners such as the PEG-150 pentaerythritol tetrastearate may be effectively employed in preparing the clear antiperspirant compositions in accordance with the present invention. Preferably from about 1.5 to about 2.0 wt. % of PEG-150 pentaerythritol tetrastearate will be employed in producing the preferred clear antiperspirant microemulsion compositions of the present invention.

To further enhance the overall feel and cosmetic appeal of the antiperspirant compositions of the present invention, it has been found that the addition of an oil-in-water in-water emulsifying system comprising a polyoxyethylene, polyoxypropylene block polymer in combination with glycereth-7-benzoate and a nonionic surfactant to provide high temperature stability may be effectively employed.

Preferably the polyoxyethylene, polyoxypropylene block polymer employed will be Poloxamer 217, which is a commercially available material which will be known to those skilled in the art and is available from BASF-Wyandotte.

Generally the preferred Poloxamer 217 component of the oil-in-water emulsifying system which is preferably used in preparing the preferred embodiments of the present invention will be present in amounts from about 0.5 to about 2.0 wt. % and will preferably be present in amounts of about 1 wt. % based upon the total weight of the resultant clear antiperspirant microemulsion product.

The glycereth-7-benzoate component of the oil-in-water emulsifying system is a known ingredient which is commercially available and is the benzoated derivative of a polyethylene glycol ether of glycerin.

Generally speaking, from about 0.5 to 2 % by weight of the glycereth-7-benzoate component of the oil-in-water emulsifying system has been found to be effective in producing a satisfactory resultant clear antiperspirant microemulsion. Preferably about 1 wt.% of glycereth-7-benzoate will be employed.

The nonionic surfactant component of the oil-in-water emulsifying system will generally be present in amounts less than 5 wt. % and will preferably be selected from octoxynol-9 (Polyoxyethylene(9) Octyl Phenyl Ether and lauricdiethanolamide. These materials are also known commercially available materials as will be recognized by those skilled in the art. Preferably when the nonionic surfactant is octoxynol-9 or lauricdiethanolamide, this ingredient will be present in an amount of from about 1 to about 2 wt. % based upon the total weight of the resulting clear antiperspirant microemulsion produced.

The soluble electrolyte component which may be added to further control the viscosity and to enhance clarity will preferably be sodium chloride.

It has been found that from about 0.01 to about 0.5 wt. % of soluble electrolyte may be effectively employed. When the soluble electrolyte is the preferred sodium chloride it has been found that from about 0.10 to about 0.13 wt. % may be preferably used in order to provide the degree of viscosity control and clarity enhancement sought.

It has also been found that the use of a humectant to enhance low temperature stability such as for instance a mono- or dialkylene glycol of up to eight carbon atoms, which will preferably be dipropylene glycol, may be effectively employed in producing the preferred clear antiperspirant microemulsion of the present invention.

Generally speaking, the mono- or dialkylene glycol component may be effectively employed in amounts of from about 0.1 to about 10 wt. % and will preferably be present in amount of about 7 to about 9 wt. % and most preferably in amounts of about 8 wt. % based upon the total weight of the resultant clear antiperspirant microemulsion product.

Various optional ingredients such as perfumes fillers and the like may also be added to the clear antiperspirant microemulsion compositions of the present invention as will be understood by those skilled in the art. Typically where such ingredients are utilized they will be each present in amounts of from about 0.05 to about 1.0 wt. % based upon the total weight of the resultant clear antiperspirant microemulsion composition produced, to provide their art recognized function. Preferably where a perfume component is utilized, about 0.5 wt. % will be employed.

The foregoing more general discussion of the present invention will be further illustrated by the following specific examples.

EXAMPLES

General

Unless otherwise indicated in a specific example the antiperspirant compositions were prepared using the following general procedure, which is inclusive of all components which may be utilized. For those formulations where less than all of the components are employed, the following procedure was suitably modified to eliminate that component, or components, of the formulation not called for.

General Procedure

Preparation of Water Phase

1. In a suitable vessel, equipped with a homo-mixer, add the formula weight of antiperspirant active in solution, dipropylene glycol, deionized water and sodium chloride. Heat the solution with mixing to 110° F.–120° F.

Preparation of Oil Phase

2. In a separate steam jacket vessel add Cetiol HE, isopropyl myristate, octoxynol-9 (Polyoxyethylene(9) Octyl Phenyl Ether) and glycereth-7-benzoate, and begin to heat with suitable mixing to 140° F.–145° F.

3. To step (2) add PEG-150 pentaerythritol tetrastearate with continued mixing.

4. To step (3) add Poloxamer 217 (polyoxyethylene, polyoxypropylene block polymer of the general formula $$HO(CH_2CH_2O)_x(CHCH_2O)_y(CH_2CH_2O)_zH$$
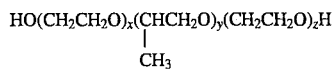

in which the average values of x, y, and x are respectively 52, 35 and 52) with continued mixing.

5. To step (4) add cyclomethicone D-5 with continued mixing.

6. Mix until homogeneous maintaining temperature between 140° F.–145° F.

Preparation of Combined Phases

7. Transfer the oil phase to the water phase with homo-mixing.

8. Continue homogenization and cool the batch to 70°–72° F.

9. To step (8), add perfume with mixing until homogeneous.

10. Take the viscosity at 70°–72° F. If the viscosity is within 1,000±200 cps q.s. with water to 100%. If not proceed to step (11).

11. Adjust the viscosity by adding melted PEG-150 pentaerythritol tetrastearate (Crothix) and sodium chloride in increments of 0.17 wt. % and 0.03 wt. % respectively with mixing until the viscosity is within specification or the maximum level of Crothix and sodium chloride is reached.

Example I

A composition in accordance with the present invention was prepared by admixing the following ingredients in accordance with the general procedure given above, in the proportions indicated.

| Ingredient | Parts By Weight |
| --- | --- |
| Aluminum Zirconium Tetrachlorohydrex Gly, 35% (Rezal 36 G Soln.) Reheis | 50.00 |
| PEG-7-glyceryl cocoate (Cetiol HE) Henkel | 18.00 |
| Deionized Water | 10.90 |
| Cyclomethicone D-5 | 5.00 |
| Isopropyl Myristate | 2.00 |

Upon evaluation, the foregoing composition was found to be clear and after application to the human skin to dry without leaving a white residue.

Example II

A composition not in accordance with the present invention was prepared by admixing the following ingredients in accordance with the general procedure given above, in the proportions indicated.

| Ingredient | Parts By Weight |
| --- | --- |
| Aluminum Zirconium Tetrachlorohydrex Gly, 35% (Rezal 36 G Soln.) Reheis | 50.00 |
| Deionized Water | 10.90 |
| Cyclomethicone D-5 | 5.00 |
| Isopropyl Myristate | 2.00 |

Upon evaluation, the foregoing composition was found to separate thereby indicating that the presence of PEG-7-glyceryl cocoate is essential to obtaining a clear composition.

Example III

A composition in accordance with the present invention was prepared by admixing the following ingredients in accordance with the general procedure given above, in the proportions indicated.

| Ingredient | Parts By Weight |
| --- | --- |
| Aluminum Zirconium Tetrachlorohydrex Gly, 35% (Rezal 36 G Soln.) Reheis | 50.00 |
| PEG-7-glyceryl cocoate (Cetiol HE) Henkel | 18.00 |
| Deionized Water | 10.90 |
| Cyclomethicone D-5 | 5.00 |

Upon evaluation, the foregoing composition was found to be clear which again is attributed to the presence of the PEG-7-glyceryl cocoate component.

Example IV

A composition was prepared by admixing the following ingredients in accordance with the general procedure given above, in the proportions indicated.

| Ingredient | % (W/W) |
| --- | --- |
| Aluminum Zirconium Tetrachlorohydrex Gly, 35% (Rezal 36 G Soln.) Reheis | 50.00 |
| PEG-7-glyceryl cocoate (Cetiol HE) Henkel | 18.00 |
| Deionized Water | 10.37–10.90 |
| Cyclomethicone D-5 | 5.00 |
| Dipropylene glycol (low odor grade) | 8.00 |
| Isopropyl Myristate | 2.00 |
| Octoxynol-9 (Triton X-100) Union Carbide | 2.00 |
| PEG-150 Pentaerythritol Tetrastearate (Crothix) Croda | 1.50–2.00 |
| Poloxamer 217 (polyoxyethylene, polyoxypropylene block polymer of the general formula $$HO(CH_2CH_2O)_x(CHCH_2O)_y(CH_2CH_2O)_zH$$ \| CH₃ in which the average values of x, y, and z are | 1.00 |

| Ingredient | % (W/W) |
| --- | --- |
| respectively 52, 35 and 52) (Pluracare F-77) BASF | |
| Glycereth-7-benzoate (Dermol G-76) Alzo | 1.00 |
| Perfume | 0.50 |
| Sodium Chloride | 0.10–0.13 |
| | 100.00 |

Upon evaluation, the foregoing composition was found to be clear and upon drying after application to human skin was found to leave no visible white residue.

In addition, the antiperspirant composition of this example was found to impart a highly acceptable feel which proved to be appealing to the user.

Example V

A composition was prepared by admixing the following ingredients in accordance with the general procedure given above, in the proportions indicated.

| Ingredient | % (W/W) |
| --- | --- |
| Aluminum Chlorohydrate Tetrachlorohydrex Gly, 35% (Rezal 36 G Soln.) Reheis | 50.00 |
| PEG-7-Glyceryl Cocoate (Cetiol HE) | 18.00 |
| Deionized Water | 11.40 |
| Cyclomethicone D-5 | 5.00 |
| Isopropyl Myristate | 2.00 |
| Triton X-100 (Octoxynol-9) Union Carbide | 2.00 |
| PEG-150 Pentaerythritol Tetrastearate (Crothix) Croda | 1.50 |
| Poloxamer 217 (polyoxyethylene, polyoxypropylene block polymer of the general formula 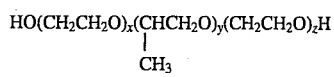 in which the average values of x, y, and z are respectively 52, 35 and 52) (Pluracare F-77) BASF | 1.00 |
| Glycereth-7-Benzoate (Dermol G-76) Alzo | 1.00 |
| Sodium Chloride | 0.10 |
| Dipropylene Glycol (low odor grade) | 8.00 |
| | 100.00 |

Upon evaluation, the foregoing composition was found to be clear and upon drying after application to human skin was found to leave no visible white residue.

In addition, the antiperspirant composition of this example was found to impart a highly acceptable feel which proved to be appealing to the user.

While a limited number of preferred embodiments of the present invention have been described and tested above, one skilled in the art will, nevertheless, recognize numerous substitution, modifications and alterations which can be made without departing from the spirit and scope of the invention as limited by the following claims.

I claim:

1. A clear, low residue antiperspirant composition comprising on a weight basis from about 5 to about 30% antiperspirant active; from about 5 to about 25% PEG-7-glyceryl cocoate; from about 0.5 to about 3% emollient; from about 3 to about 7% cyclomethicone and from about 35 to 60% water, said antiperspirant composition being in the form of an oil-in-water microemulsion.

2. A composition according to claim 1, wherein the antiperspirant active component is selected from the group consisting of aluminum zirconium tetrachlorohydrex GLY and aluminum chlorohydrate.

3. A composition according to claim 1, wherein the emollient material is a liquid fatty acid ester.

4. A composition according to claim 1, wherein the emollient material is isopropyl myristate.

5. A composition according to claim 1, which also contains an organic nonresinous thickener.

6. A composition according to claim 5, wherein the organic nonresinous thickener is PEG-150 pentaerythritol tetrastearate.

7. A composition according to claim 5, wherein the organic nonresinous thickener is present in an amount of from about 0.1 to about 3 wt. %.

8. A composition according to claim 6, wherein the PEG-150 pentaerythritol tetrastearate is present in an amount of about 1.5 to 2 wt. %.

9. A composition according to claim 1, which also comprises an oil-in-water emulsifying system.

10. A composition according to claim 9, wherein the oil-in-water emulsifying system comprises Poloxamer 217, (polyoxyethylene, polyoxypropylene block polymer of the general formula

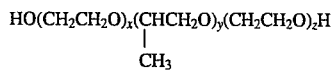

in which the average values of x, y, and z are respectively 52, 35 and 52) glycereth-7-benzoate and a nonionic surfactant.

11. A composition according to claim 10, wherein the nonionic surfactant is selected from the group consisting of octoxynol-9 (polyoxyethylene (9) octyl phenyl ether) and lauricdiethanolamide.

12. A composition according to claim 10, wherein the Poloxomer 217 (polyoxyethylene, polyoxypropylene block polymer of the general formula $$HO(CH_2CH_2O)_x(CHCH_2O)_y(CH_2CH_2O)_zH$$
$$|$$
$$CH_3$$

in which the average values of x, y, and z are respectively 52, 35 and 52) is present in an amount of about 0.5 to about 2 wt. %;

the glycereth-7-benzoate is present in an amount of from about 0.5 to about 2 wt. %, and the nonionic surfactant is present in a definite amount less than 5 wt. %.

13. A composition according to claim 1 which also comprises a soluble electrolyte as a viscosity control agent.

14. A composition according to claim 13, wherein the soluble electrolyte is sodium chloride.

15. A composition according to claim 13, wherein the sodium chloride is present in an amount of from about 0.01 to about 0.5 wt. %.

16. A composition according to claim 1, which also comprises a combination of PEG-150 pentaerythritol tetrastearate and sodium chloride.

17. A composition according to claim 1, which also comprises a humectant to impart low temperature stability.

18. A composition according to claim 17, wherein the humectant is a mono- or dialkylene glycol of up to 8 carbon atoms.

19. A composition according to claim 17, wherein the humectant is dipropylene glycol.

20. A composition according to claim 17, wherein the humectant is present in an amount of from about 0.5 to about 10 wt. %.

21. A composition according to claim 17, wherein the humectant is dipropylene glycol which is present in an amount of about 8 wt. %.

22. A composition according to claim 1, which also comprises one or more of the following ingredients present in an amount of from 0.01 to about 1.0 wt. %: perfumes and fillers.

23. A composition according to claim 22, wherein the ingredients are perfumes which are present in an amount of about 0.50 wt. %.

24. A clear low residue oil-in-water microemulsion based antiperspirant composition comprising:

| | |
|---|---|
| 50 parts by weight | Aluminum Zirconium Tetrachlorohydrex Gly (35% solution in water) |
| 18 parts by weight | PEG-7-glyceryl cocoate |
| 10.90 parts by weight | Deionized Water |
| 5.00 parts by weight | Cyclomethicone |
| 2.00 parts by weight | Isopropyl Myristate |

25. A clear oil-in-water microemulsion based antiperspirant composition comprising:

| | |
|---|---|
| 50.00 wt. % | Aluminum Zirconium Tetrachlorohydrex Gly (35% solution in water) |
| 18.00 wt. % | PEG-7-glyceryl cocoate |
| 10.37–10.90 wt. % | Deionized Water |
| 5.00 wt. % | Cyclomethicone |
| 2.00 wt. % | Isopropyl Myristate |
| 2.00 wt. % | Octoxynol-9 (Polyoxyethylene(9) Octyl Phenyl Ether) |
| 1.50–2.00 wt. % | PEG-150 Pentaerythritol Tetrastearate |
| 1.00 wt. % | Poloxamer 217 (polyoxyethylene, polyoxypropylene block polymer of the general formula $HO(CH_2CH_2O)_x(CHCH_2O)_y(CH_2CH_2O)_zH$ with a $CH_3$ branch, in which the average values of x, y, and z are respectively 52, 35 and 52) |
| 1.00 wt. % | Glycereth-7-benzoate |
| 0.10–0.13 wt. % | Sodium Chloride. |

26. A clear low residue oil-in-water microemulsion based antiperspirant composition comprising:

| | |
|---|---|
| 50.00 wt. % | Aluminum Chlorohydrate Tetrachlorohydrex Gly (35% solution in water) |
| 18.00 wt. % | PEG-7-Glyceryl Cocoate |
| 11.40 wt. % | Deionized Water |
| 5.00 wt. % | Cyclomethicone |
| 2.00 wt. % | Isopropyl Myristate |
| 2.00 wt. % | Octoxynol-9 (Polyoxyethylene(9) Octyl Phenyl Ether) |
| 1.50 wt. % | PEG-150 Pentaerythritol Tetrastearate |
| 1.00 wt. % | Poloxamer 217 (polyoxyethylene, polyoxypropylene block polymer of the general formula $HO(CH_2CH_2O)_x(CHCH_2O)_y(CH_2CH_2O)_zH$ with a $CH_3$ branch, in which the average values of x, y, and z are respectively 52, 35 and 52) |
| 1.00 wt. % | Glycereth-7-Benzoate |
| 0.10 wt. % | Sodium Chloride |
| 8.00 wt. % | Dipropylene Glycol. |

* * * * *